(12) United States Patent
Xu et al.

(10) Patent No.: US 8,570,027 B2
(45) Date of Patent: Oct. 29, 2013

(54) HIGH RESOLUTION SCANNING MAGNETIC IMAGING METHOD WITH LONG DETECTION RANGES

(75) Inventors: Shoujun Xu, Houston, TX (US); Li Yao, Houston, TX (US)

(73) Assignee: University of Houston System, Houston, TX (US)

( * ) Notice: Subject to any disclaimer, the term of this patent is extended or adjusted under 35 U.S.C. 154(b) by 579 days.

(21) Appl. No.: 12/791,763

(22) Filed: Jun. 1, 2010

(65) Prior Publication Data

US 2010/0301849 A1     Dec. 2, 2010

Related U.S. Application Data

(60) Provisional application No. 61/182,913, filed on Jun. 1, 2009.

(51) Int. Cl.
*G01N 27/74*      (2006.01)

(52) U.S. Cl.
USPC ........... 324/204; 600/409; 600/420; 977/958; 977/960

(58) Field of Classification Search
USPC .......... 324/204, 214, 244, 248; 600/409, 420; 977/958, 960
See application file for complete search history.

(56) References Cited

U.S. PATENT DOCUMENTS

| | | | |
|---|---|---|---|
| 2010/0176807 A1* | 7/2010 | Duric et al. | 324/228 |
| 2010/0259254 A1* | 10/2010 | Verschuren et al. | 324/244 |
| 2011/0221438 A1* | 9/2011 | Goodwill et al. | 324/301 |
| 2012/0035458 A1* | 2/2012 | Flynn | 600/409 |

* cited by examiner

*Primary Examiner* — Jay Patidar
(74) *Attorney, Agent, or Firm* — Conley Rose, P.C.

(57) ABSTRACT

A method of magnetic imaging at long detection ranges. In one embodiment the method comprises introducing a magnetic sample having magnetic particles into a detection field; detecting weak magnetic field signals of the magnetic particles; forming an image from the detected signals; and determining the location and quantity amount of the magnetic particles. The method further comprises introducing a magnetic sample to a human or other organism's body.

16 Claims, 7 Drawing Sheets

| Stage (mm)[a] | d (mm) | Δd (mm) | M ($10^{-10}$ A·m$^2$) |
|---|---|---|---|
| 0 | 6.304 ± 0.020 | 0 | 5.353 ± 0.049 |
| 0.100 | 6.408 ± 0.020 | 0.104 | 5.415 ± 0.048 |
| 0.200 | 6.519 ± 0.023 | 0.215 | 5.505 ± 0.054 |
| 0.300 | 6.616 ± 0.022 | 0.311 | 5.551 ± 0.051 |
| 0.400 | 6.709 ± 0.020 | 0.405 | 5.589 ± 0.047 |

[a] The stage positions are relative values to the position of the first measurement, which is set as 0.

FIG. 6

| Scan Number | 1 | 2 | 3 | 4 | 5 |
|---|---|---|---|---|---|
| Stage[a] [mm] | 0 | 0.100 | 0.200 | 0.300 | 0.400 |
| $d_1$ [mm] | 6.677 (0.019) | 6.774 (0.018) | 6.864 (0.023) | 6.973 (0.024) | 7.073 (0.022) |
| $\Delta d_1$[a] [mm] | 0 | 0.097 | 0.187 | 0.296 | 0.395 |
| $x_1$ [mm] | 66.47 (0.01) | 66.61 (0.01) | 66.60 (0.02) | 66.64 (0.02) | 66.60 (0.02) |
| $M_1$ [$10^{-10}$ A·m$^2$] | 1.667 (0.014) | 1.571 (0.013) | 1.505 (0.016) | 1.466 (0.016) | 1.442 (0.014) |
| $\theta_1$ [degree] | 63 | 61 | 60 | 58 | 59 |
| $d_2$ [mm] | 6.779 (0.024) | 6.873 (0.024) | 6.970 (0.022) | 7.070 (0.021) | 7.175 (0.025) |
| $\Delta d_2$[a] [mm] | 0 | 0.094 | 0.192 | 0.291 | 0.396 |
| $x_2$ [mm] | 106.77 (0.02) | 106.56 (0.02) | 106.82 (0.02) | 106.79 (0.02) | 106.65 (0.02) |
| $M_2$ [$10^{-10}$ A·m$^2$] | 1.633 (0.018) | 1.520 (0.016) | 1.472 (0.015) | 1.446 (0.013) | 1.436 (0.015) |
| $\theta_2$ [degree] | 66 | 69 | 63 | 63 | 66 |
| $x_2 - x_1$ [mm] | 40.29 | 39.95 | 40.22 | 40.14 | 40.06 |
| $d_2 - d_1$ [mm] | 0.102 | 0.099 | 0.107 | 0.097 | 0.102 |
| $M_1/M_2$ | 1.02 | 1.03 | 1.02 | 1.01 | 1.00 |

[a] Relative values to the first measurement, which is set as 0.

FIG. 7

HIGH RESOLUTION SCANNING MAGNETIC IMAGING METHOD WITH LONG DETECTION RANGES

CROSS-REFERENCE TO RELATED APPLICATIONS

This application claims the benefit under 35 U.S.C. §119 (e) of U.S. Provisional Patent Application No. 61/182,913 filed Jun. 1, 2009, the disclosure of which is hereby incorporated herein by reference.

STATEMENT REGARDING FEDERALLY SPONSORED RESEARCH OR DEVELOPMENT

Not applicable.

BACKGROUND

1. Field of the Invention

The present invention relates to the design and use of a novel scanning magnetic imaging method with high resolution and long detection range.

2. Background

Magnetic nanoparticles are widely used as biochemical markers, drug-delivery carriers and imaging contrast agents. Moreover, micrometer- and nanometer-sized particles are commonly used in biochemical assays as a means to capture, concentrate, and manipulate target analytes and increasingly so as detection labels for assay readout. These detection applications benefit from the relatively large magnetic field signature generated by the beads when magnetized by an applied magnetic field, and from the very low incidence of background magnetic signals. These features altogether make magnetic detection an attractive technology for a range of biochemical analysis.

However, the precise determination of the position and number of particles at a given time is vital for these purposes. In many applications, such as assay analysis on microchips and in vivo imaging, the magnetic particles are far from the detectors, on the order of several millimeters to a few centimeters. This makes it challenging to obtain desired spatial information and sufficient detection limit because of the $r^{-3}$ dependence of magnetic field strength, where r is the distance between the sample and the detector.

Successful imaging of magnetic nanoparticles in practical settings requires two criteria. One is high sensitivity in directly detecting magnetic fields. The other is the capability of resolving spatial information at a long detection distance. Various magnetic force microscopy and magnetic resonance force microscopy techniques, which usually have a detection range of around a few nanometers or less, are thus not suitable for those applications. Similarly, room-temperature giant magneto-resistive sensors are only applicable when the sensor is placed within a few micrometers of the sample. Large-scale magnetic imaging modalities often lack sensitivity because of the distance dependence of the magnetic field and magnetic response; the degraded sensitivity requires the use of impractical amounts of sample. Indirect detection of magnetic particles has also been investigated. Optical detection offers high sensitivity, but it requires a transparent environment, which cannot be satisfied in many cases. Separately, conventional magnetic resonance imaging offers high spatial resolution via encoding with gradient magnetic fields, but with drawbacks including poor sensitivity to dc magnetic field and the requirement of a superconducting magnet.

Atomic magnetometers have also been used to detect magnetic particles; however, no spatial information was extracted, nor could the amount of the sample be determined. Since magnetic field is a function of both the number of nanoparticles and their distance to the detector, it is difficult to resolve spatial information without prior knowledge of the amount of the sample.

A similar situation is encountered during imaging of biological magnetic fields, for example, the magnetic fields from human brain or heart. The magnetic field strength is determined by both the amplitude of the magnetic source and its distance to the detectors. With one measurement or a few measurements, it is difficult to simultaneously localize the source of the magnetic field and reveal its strength.

It is therefore the purpose of the present invention to develop a scanning imaging method to generate a two-dimensional or three-dimensional map of the magnetic fields.

SUMMARY OF THE INVENTION

A method for scanning magnetic imaging which, comprising: introducing a magnetic sample having magnetic particles into a detection field; detecting weak magnetic field signals of the magnetic particles; forming an image from the detected signals; and determining the location and quantity amount of the magnetic particles. The method further comprises introducing a magnetic sample to a human or other organism's body.

These and other embodiments, features, and advantages will be apparent in the following detailed description and drawings.

BRIEF DESCRIPTION OF THE DRAWINGS

FIG. 6 shows TABLE 1, the comparison between the stage movement and fitted distance values, d, and measured magnetization results, M.

FIG. 7 shows TABLE 2, the results for the five scans of multi-sample scanning magnetic imaging, and comparison of the fitted d- and x-coordinate differences with stage movements and the numbers in parentheses are the fitting errors.

DETAILED DESCRIPTION OF THE PREFERRED EMBODIMENTS

The technique of this disclosure finds many applications which include but are not limited to homeland security applications such as the detection bacteria and infectious diseases, monitoring of various toxins or toxic chemicals in soil, water and air; to industrial applications such as the non-destructive detection of subsurface trace magnetic particles in products; to lab-on-the-chip reactions and micro-fluidics that involve magnetically labeled chemical and biological entities; imaging of biological magnetic fields from brain and heart; and in vivo imaging of magnetic particles used for disease diagnosis. By using the full magnetic field profile, instead of a single point measurement, the present disclosure allows resolution of the spatial information while quantifying the amount of the magnetic sample simultaneously. Furthermore, it is possible to perform a series of scans to obtain an image of one or multiple magnetic samples, which demonstrates the accuracy of the distance measurement and the reproducibility of the measured amount of the magnetic sample.

Figure 1:
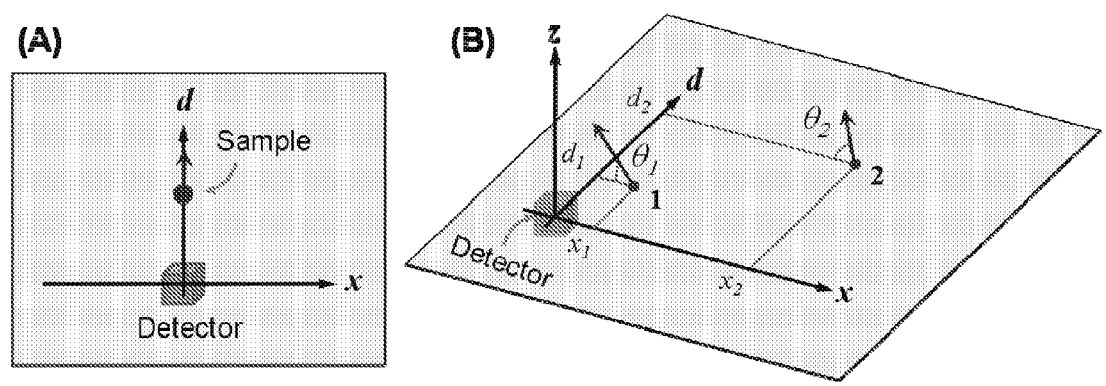
FIG. 1A, illustrates a magnetic sample that is located far from the detector, with a distance on the order of millimeters to tens of centimeters.
FIG. 1B illustrates a general case when multiple magnetic entities (1 and 2) with arbitrary magnetic orientation located at positions with coordinates $(x_1, d_1)$ and $(x_2, d_2)$ respectively and wherein the magnetic orientations are indicated by arrows.
Figure 2:
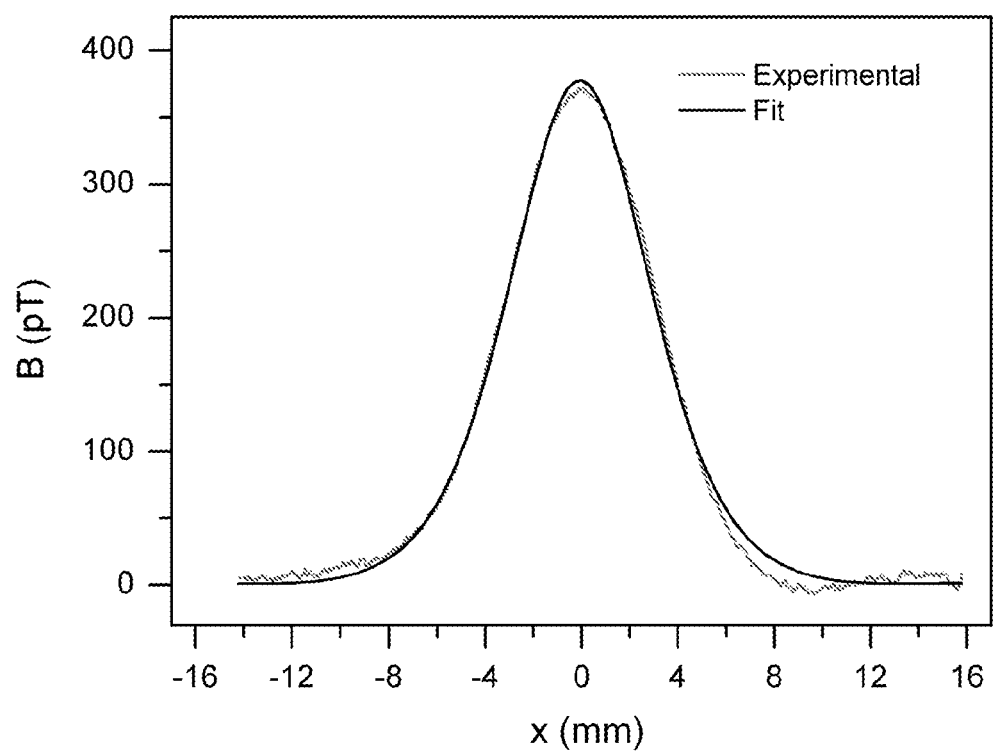
FIG. 2 illustrates the magnetic field profile of an assembly of about $7 \times 10^5$ magnetic nanoparticles. The gray trace is experimental data, and the black trace is the fit to reveal spatial information and the quantity of the particles.

FIG. 1 shows an experimental configuration for the present disclosure. The detector, for example without limitation a cesium-based atomic magnetometer, is located several millimeters away from an assembly of magnetic nanoparticles to be measured. The magnetic sample can be scanned both perpendicular to the propagation or direction of the laser along the x-axis and parallel to the laser along the d-axis. The detector measures the magnetic field generated by the nanoparticles at each position during the scans. FIG. 1A illustrates a single sample and FIG. 1B shows a representative instance with multiple samples. The result for a single scan along the x direction of a single sample is shown in FIG. 2.

Without prior knowledge on the precise amount of the sample or its distance to the detector, the present process allows determination both the spatial information and the amount of the magnetic sample. Based on the experimental geometry and since the magnetic field corresponds to the overall dipolar field of the sample particles, the profile follows Equation 1:

$$B = B_0 + \frac{\mu_0 M}{4\pi((x-x_0)^2 + d^2)^{3/2}} \left( 3\frac{d^2}{(x-x_0)^2 + d^2} - 1 \right) \quad (1)$$

In Equation 1, B is the magnetic field measured by the magnetometer, and $B_0$ is the baseline correction or a constant applied magnetic field. The symbol x represents a position on the x-axis and $x_0$ represents the position on the x axis that corresponds to the maximum signal, which is normalized to zero in the figure for convenience. M is the magnetization of the magnetic particles, and d is the distance between the sample and the detector. By performing a least-square fit on the magnetic field profile, it is possible to obtain the magnetization of the particles and the distance between the sample and the detector. The values are $(5.589 \pm 0.047) \times 10^{-10}$ A·m² and $6.709 \pm 0.020$ mm, respectively.

An atomic magnetometer is used as the detector for demonstration of this invention. It is based on the D1 transition (894.5952 nm) of cesium atoms that are contained in a cubic cell with a volume of 125 µl. A capillary loaded with about 30 nl of amine-coated magnetic particles is placed on a sample holder, which is located several millimeters from the atomic detector. The number of the magnetic particles is estimated to be $7 \times 10^5$ from the concentration of the particles. Prior to the measurements, the magnetic nanoparticles are magnetized by approaching the pole face of a permanent magnet vertically. The motion of the sample is achieved by using an automated linear actuator for x-axis scans and a pair of motorized nano-positioning stages for d-axis movements. The magnetic field from the sample is measured by monitoring the magneto-optical resonance on the polarization rotation of the laser beam. The sensitivity of the atomic magnetometer is about 200 fT/(Hz)$^{1/2}$ (fT: femtotesla, $10^{-15}$ Tesla). In instances, the integration time for each data point is about 30 ms.

Figure 3:
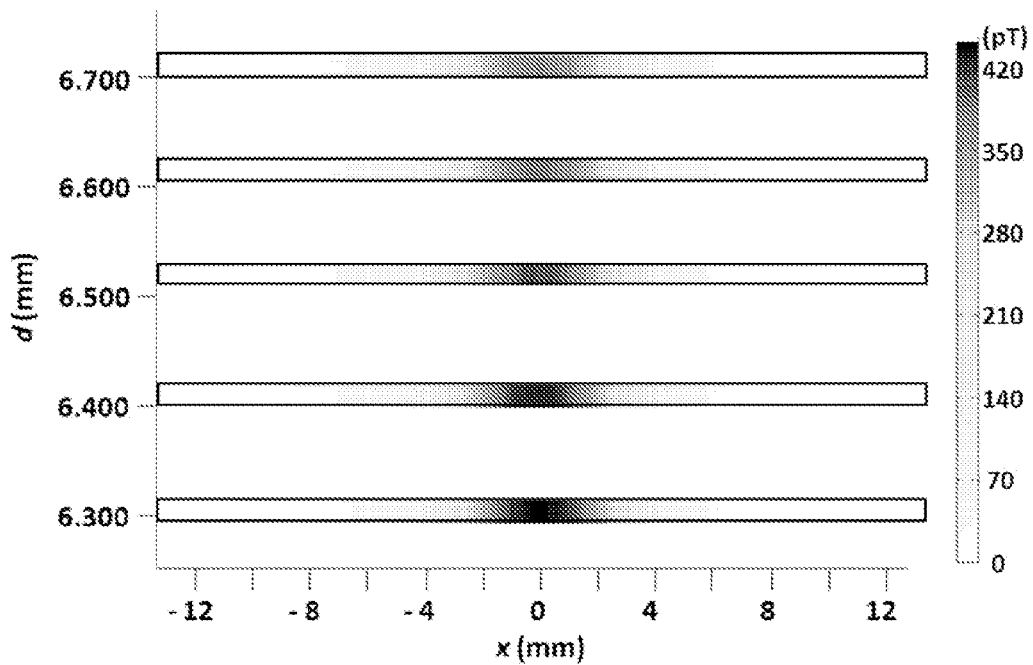
FIG. 3 illustrates a two-dimensional scanning magnetic image, where each stripe represents an x-axis scan and the width of each stripe is determined by the corresponding error bar of the fitted d value.

To demonstrate two-dimensional scanning imaging, a series of x-axis scans at different distances is performed and illustrated in FIG. 3. The X-axis scanning may be along a path, such that the scanning comprises a path chosen from the group consisting of: a straight line, a parabolic path, a curve, or combinations thereof. The d values are varied in increments of 100 µm by moving the nano-positioning stages that hold the sample. Alternatively, translation stages, linear actuators, precision pumps, or combination thereof may be used. magnetic field is a function of both the x position, which is controlled by a linear actuator, and the d position, which is obtained from the experimental magnetic profile. The maximum value of the magnetic field, for instance at x=0, decreases as the sample moves farther from the detector. Due to the small amount of the sample and the large separation between the sample and the detector, the amplitude of the signal is about several hundreds of pico-tesla, which is much smaller than the signal in magnetic force microscopy.

From the two-dimensional image as shown in FIG. 3, it is possible to examine the accuracy of the d-parameters obtained from fitting the magnetic field profile as in FIG. 3. The fitted d values are additionally listed in Table 1, along with the readings from the nano-positioning stages for comparison. The error bars are all less than about 23 µm. Importantly, from the relative distance movement Δd, the values obtained from the image agree well with the readings from the nano-positioning stages. In this instance, the accuracy is within about 15 µm.

Figure 4:
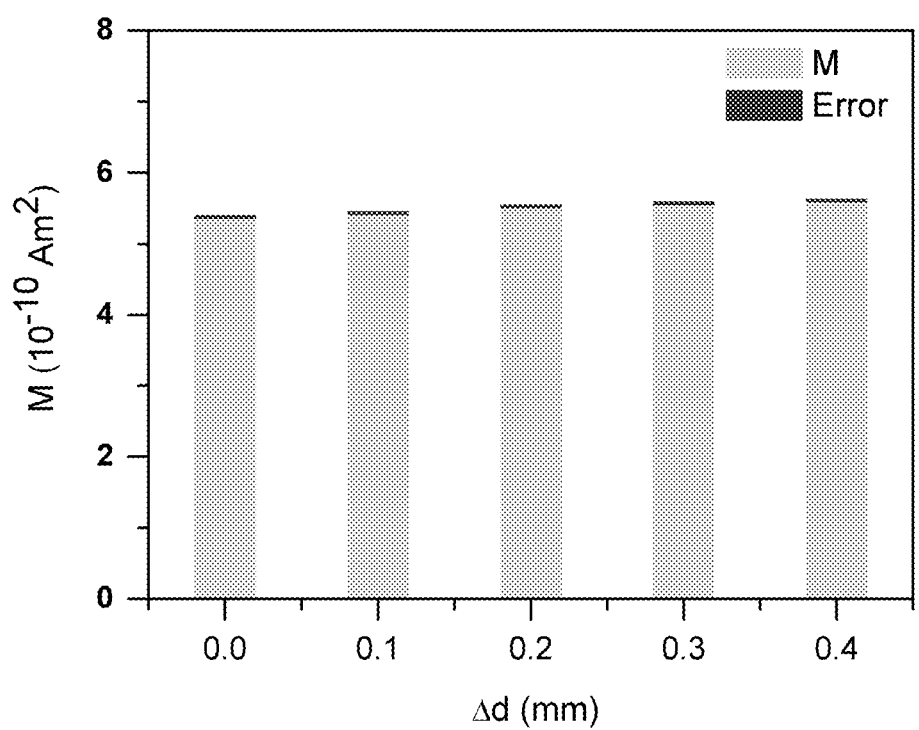
FIG. 4 illustrates the fitted magnetizations of the sample for the different x scans which are indicated using relative distances, Δd and the respective error bars are plotted on top of their corresponding magnetization values.

In addition to the spatial information, the magnetization values obtained from different x-axis scans are compared. Since the imaging scans are performed with a fixed number of magnetic particles, the magnetization obtained at different distances should be the same (within experimental error). FIG. 4 plots the resulting M values as a function of relative distance Δd which represents different x-scans. For each point, the error bar is within about 1%. The average magnetization for the five x-scans is $5.483 \times 10^{-10}$ A·m², with a standard deviation of $0.097 \times 10^{-10}$ A·m², which is less than about 1.8% of the average.

The present disclosure demonstrates that at a detection distance up to about 6.7 mm this process can achieve a spatial resolution of about 23 µm. The magnetization, and hence the amount of nanoparticles, is accurate within about 1.8% for about 30 nl of the sample. This indicates a detection limit of about 500 picoliter (picoliter: $10^{-12}$ liter) of the sample being used, as in this process. As such, the disclosure, having micrometer resolution and sub-nanoliter detection limits, has the potential to fill the gap between microscopic magnetic imaging and long-distance magnetic sensing.

Further, the intrinsic sensitivity of the atomic magnetometer, with a given size of about 125 µl and a fixed operating temperature of about 37° C., can be estimated. Based on theoretical modeling, the sensitivity of the present process can reach 1 fT/(Hz)$^{1/2}$ when spin-exchange relaxation between atoms is the limiting de-coherence factor, and 0.1

$fT/(Hz)^{1/2}$ when the magnetometer is operated in a spin-exchange relaxation-free regime. A 0.1 $fT/(Hz)^{1/2}$ sensitivity will lead to a spatial resolution of 2 μm or a detection limit of a few hundred of magnetic nanoparticles, which corresponds to several zeptomoles (zeptomole: $10^{-21}$ mole) of magnetically-labeled biochemical entities.

Figure 5:
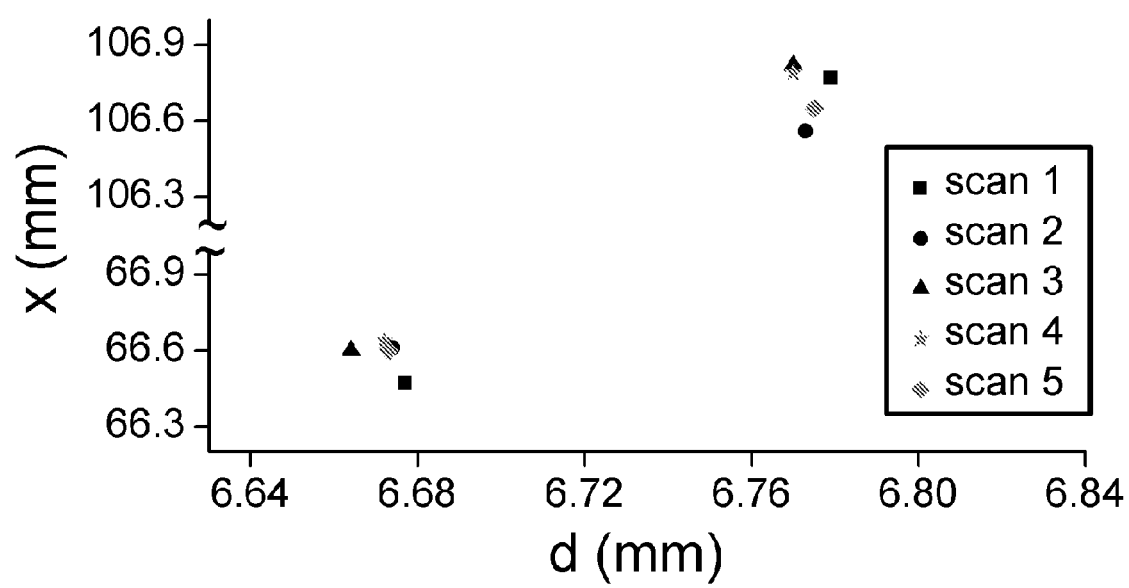
FIG. 5 illustrates the imaging of multiple magnetic entities as shown in FIG. 1B, where five scans are performed to demonstrate the spatial precision; the scans are conducted with sequential shift along the d-axis of 100 μm which is controlled by translation stages and this movement is subtracted from the corresponding fitted d-values before overlaying the five scans.

For a general case where multiple magnetic samples are present, as shown in FIG. 1 (B), the results are shown in FIG. 5. Five scans along the x-axis are obtained, with an offset of 100 along the d-axis between consecutive scans, in order to demonstrate the spatial precision. Since the magnetic orientation of the samples are unknown, the equation for dipolar magnetic field is modified as in Equation 2:

$$B_i = \frac{\mu_0 M_i}{4\pi((x-x_i)^2 + d_i^2)^{3/2}} \left( \frac{3a_i d_i^2}{(x-x_i)^2 + d_i^2} + 3\sqrt{1-a_i^2} \frac{(x-x_i)d_i}{(x-x_i)^2 + d_i^2} - a_i \right), \quad (2)$$

$$i = 1, 2.$$

The modification is the magnetic dipole parameter $a_i$, with $a_i = \cos \theta_i$, in which $\theta_i$ is the angle between the corresponding magnetic dipole and the detection axis of the magnetometer. The fitted results are shown in Table 2. The spatial resolutions are 20 μm for the d-axis and 200 μm for the x-axis. The resolutions may be improved by using a detector with better sensitivity.

For three-dimensional imaging, the z-axis is equivalent to the x-axis, both of which are perpendicular to the d-axis. Therefore, by using this process along both the x- and z-axes, three-dimensional imaging is possible. Further, for applications in which the sample must be stationary (e.g., when large biomedical systems or geophysical objects are involved), imaging can be achieved by scanning the magnetometer. It is also possible to assemble a two-dimensional array for better signal-to-noise ratio and detection efficiency, especially when multiple samples are being imaged. Three-dimensional magnetic imaging is also possible with a scanning magnetometer array.

This disclosure presents a novel process for magnetic imaging applications: magnetic nanoparticles useful in practical applications can be imaged with high resolution and low detection limit. In operation, the present disclosure details a scanning imaging method that is capable of simultaneously revealing the spatial information and amplitude of magnetic sources. The combination of a resolution of about 20 μm with a detection distance of nearly 1 cm and a detection limit in the femtotesla range makes the present invention uniquely suited for practical applications involving magnetic nanoparticles and/or imaging of faint biological magnetic signals. For instance magnetically-labeled: chemicals, biochemicals, and other biological components such as DNA, RNA, proteins, and the diseases caused by these components. Of further interest is the imaging of magnetic markers employed in lab-on-a-chip devices. Further, it is possible that the process could identify channels that contain magnetic particles and reveal the amount of magnetically labeled biochemical entities therein.

What is claimed is:

1. A method for scanning magnetic imaging which, comprising:
   introducing a magnetic sample having magnetic particles into a detection field;
   detecting weak magnetic field signals of the magnetic particles by moving the distance of the detector relative to the magnetic sample;
   forming an image from the detected signals corresponding to the distance of the detector; and
   determining the location and quantity amount of the magnetic particles.

2. The method of claim 1, wherein the detection field comprises a scanning mode having at one operation chosen from the group consisting of: the sample is scanned in the vicinity of the detector, the detector is scanned in the vicinity of the sample, or combinations thereof.

3. The method of claim 2, wherein the scanning comprises at least one component chosen from the group consisting of: translation stages, linear actuators, precision pumps, or combination thereof.

4. The method of claim 2, wherein the scanning comprises a path chosen from the group consisting of: a straight line, a parabolic path, a curve, or combinations thereof.

5. The method of claim 2, wherein the scanning is directed in the direction perpendicular to the propagation of laser along the x-axis and the z-axis, and parallel to the laser along the d-axis.

6. The method of claim 1, wherein the detecting the weak field signals of the magnetic particles comprises a range from microns to centimeters.

7. The method of claim 6 further comprises three-dimensional magnetic imaging with a scanning detector array.

8. The method of claim 6, further comprising forming a profile of the weak magnetic field signals as a function of position in the x-axis and y-axis directions and the d-axis position.

9. The method of claim 1, wherein the forming an image further comprises, constructing an image from a series of x-axis scanning profile of the magnetic sample at different d-distances relative to the magnetic detector.

10. The method of claim 1, wherein the forming an image further comprises, constructing an image from a series of d-axis position in a scanning profile of the magnetic sample at different distances relative to magnetic detector.

11. The method of claim 1, wherein determining the location and quantity amount of the magnetic particles further comprises, performing a least-square fit on the scanning profile of the magnetic field of the particles.

12. The method of claim 11, wherein the least-square fit function is based on dipolar magnetic field.

13. The method of claim 1, wherein the magnetic sample comprises at least one chose from the group consisting of magnetically-labeled chemicals, biochemicals, DNA, proteins, cells, and combinations thereof.

14. The method of claim 1, further comprising positioning the magnetic samples in microchannels.

15. The method of claim 1, further comprising detecting the magnetic samples in an organism body.

16. The method of claim 15 wherein the magnetic samples are in a human body.

* * * * *